United States Patent
Gross et al.

[11] Patent Number: 5,643,601
[45] Date of Patent: Jul. 1, 1997

[54] PHOSPHOLIPID-AND FLUOROCARBON-CONTAINING COSMETIC

[75] Inventors: Udo Gross, Berlin; Joachim Roding, Wiesbaden, both of Germany; Klaus Stanzl, White Plains, N.Y.; Leonhard Zastrow, Monaco, Monaco

[73] Assignee: Lancaster Group AG, Ludwigshafen, Germany

[21] Appl. No.: 674,849

[22] Filed: Jul. 3, 1996

Related U.S. Application Data

[63] Continuation of Ser. No. 362,505, filed as PCT/DE93/00575, Jun. 24, 1993 published as WO94/00098, Jan. 6, 1994, abandoned.

[30] Foreign Application Priority Data

Jun. 26, 1992 [DE] Germany ............... 42 21 255.3

[51] Int. Cl.$^6$ ............... A61K 9/127; A61K 7/00
[52] U.S. Cl. ............... 424/450; 424/401; 264/4.1; 264/4.3; 514/944; 514/969
[58] Field of Search ............... 424/450, 401; 264/4.1, 4.3; 514/944, 969

[56] References Cited

U.S. PATENT DOCUMENTS

| | | | |
|---|---|---|---|
| 5,061,484 | 10/1991 | Heldebrant | 424/78 |
| 5,204,112 | 4/1993 | Hope | 424/450 |
| 5,219,538 | 6/1993 | Henderson | 428/402.2 |

FOREIGN PATENT DOCUMENTS

| | | |
|---|---|---|
| 0069307 | 1/1983 | European Pat. Off. . |
| 0091313 | 10/1983 | European Pat. Off. . |
| 0105584 | 4/1984 | European Pat. Off. . |
| 8900848 | 2/1989 | WIPO . |

OTHER PUBLICATIONS

Lautenschlager Cosmetics & Toiletries 105,may 1990.

Primary Examiner—Gollamudi S. Kishore
Attorney, Agent, or Firm—Collard & Roe, P.C.

[57] ABSTRACT

The invention relates to a cosmetic for assisting the transport of oxygen in the skin, a process for its preparation and the use thereof. The problem with the known cosmetics is the inadequate oxygen supply to the skin and the adjoining tissue. The object of the invention is therefore to get through the horny layer of the skin and the epidermis by penetration processes in order to increase the oxygen concentration in the dermal area and adjoining tissue and to activate metabolic processes. According to the invention, this is effected by a cosmetic containing asymmetric lamellar aggregates, consisting of phospholipids and oxygen-laden fluorocarbon or fluorocarbon mixture, the amount of fluorocarbon being in the range from 0.2 to 100% weight/volume, in a carrier suitable for dermatological use. Preparation is effected by emulsification of the corresponding constituents, and use in ointments, creams, lotions, waters, alcoholic extracts, pastes, powders, gels, tinctures or on dressings and plasters or in a spray.

21 Claims, 2 Drawing Sheets

PHOSPHOLIPID-AND FLUOROCARBON-CONTAINING COSMETIC

This is a continuation of application Ser. No. 08/362,505 filed on Dec. 22, 1994 now abandoned, which is International Application PCT/DE93/00575 filed on 24 Jun. 1993 and which designated the U.S.

The invention relates to a cosmetic containing phospholipids and fluorocarbons and having an activity which improves the oxygen supply to the skin.

It is known to employ particular structures in the form of aqueous phospholipid liposomes as cosmetic preparations. Structure-regenerating effects and an improvement in the capacity of resistance of the skin are ascribed to the liposomes prepared from natural phospholipids, e.g. soya lecithin, having a lamellar bilayer structure corresponding to the cell membrane structure. The liposomes penetrate the horny layer and fix to weakened sites of the epidermis and improve the interstitial cell structure.

An increase in the activity of liposomes is achieved by the encapsulation of active compounds and the preparation of liposomal cosmetics. DE-A-3242385 (L'OREAL) protects a liposomal composition which in the liposome phase contains polypeptide extracts, plant extracts (almondermin) and UV light protection filters.

The company Dior markets the face gel "Capture", which contains 5% thymus extract, 1% collagen and elastin peptides and 0.1% hyaluronic acid in liposomes of 100 nm diameter made of soya lecithin. Use is effected by means of a pump dispenser.

For improved supply of the skin with oxygen, it has already been proposed to use peroxides such as hydrogen peroxide in order to stimulate the cell metabolism of the skin via the nascent oxygen formed. The considerable side effects such as the skin irritations, however, are an obstacle to use. DE-A-2534315 claimed an $O_2$-containing cosmetological formulation which is composed of an $O_2$-saturated gaseous fluorocarbon and a surfactant in aqueous phase in an aerosol container. Borgarello (EP-A-296661) developed an isotropic single phase system for the cosmetic sector, in which halogenated compounds are intended to act as oxygen carriers. A typical composition consists of 34% of a mixture of perchloro-1-butyltetrahydrofuran and polyfluoro-1-propyltetrahydrofuran, 7% isopropanol, 49% water and 10% emulsifier. The emulsifiers used are very highly surface-active fluorosurfactants, e.g. of the perfluoroalkanesulphonamide type, which are known to be extremely toxic on i.p. administration in the mouse ($LD_{50}$ 0.1 to 0.2 g/kg) and also have an irritant effect on the skin. Other possible solutions concern the use of a haemolymph extract of molluscs or of an extract of proteins and proteides from cattle spleen.

A convincing and physically detectable toning and invigoration of the skin surface cannot be achieved with the preparations and methods mentioned.

The invention is based on the object of improving the oxygen supply to the skin with the aid of a cosmetic composition containing phospholipids such that a detectable effect is achieved.

According to the invention, the phospholipid-containing cosmetic consists of asymmetric lamellar aggregates, which consist of phospholipids and oxygen-laden fluorocarbon or fluorocarbon mixture, the amount of fluorocarbon being in the range from 0.2 to 100% w/v (w/v=weight/volume), in a carrier suitable for cosmetic use.

A plurality of fluorocarbons can be employed, e.g. aliphatic straight-chain and branched fluoroalkanes, mono- or bicyclic and optionally fluoroalkyl-substituted fluorocycloalkanes, perfluorinated aliphatic or bicyclic amines, bis(perfluoroalkyl)ethenes, perfluoropolyethers or mixtures thereof. Particularly preferred fluorocarbons are those such as perfluorodecalin, F-butyltetrahydrofuran, perfluorotributylamine, perfluorooctyl bromide, bis-fluoro(butyl)ethene or bis-fluoro(hexyl)ethene or $C_6$–$C_9$-perfluoroalkanes.

The amount of fluorocarbons here is in the range from 20 to 100% w/v, preferably in the range from 40 to 100%. A particularly preferred range is that from 70 to 100% w/v.

The term "fluorocarbons" used here is understood as meaning perfluorinated or highly perfluorinated carbon compounds or mixtures, which are able to transport gases such as $O_2$ and $CO_2$. Highly fluorinated hydrocarbon compounds within the meaning of this invention are those in which most of the hydrogen atoms are replaced by fluorine atoms, so that on further replacement the capability for gas transport is not necessarily increased. This is usually achieved if approximately up to 90% of the hydrogen atoms are replaced by fluorine atoms. Preferred fluorocarbons within the meaning of the present invention are those in which at least 95% of the hydrogen atoms are replaced, more preferably 98% and most preferably 100%.

The phospholipids employed according to the invention are natural phospholipids such as soya lecithin and egg lecithin, synthetic phospholipids. In these phospholipids, the content of phosphatidylcholine according to the invention is in the range from 30 to 99% and in particular 70 to 90%.

In addition to phosphatidylcholine, lysolecithins can also be present in the concentration range from 0.1 to 10% by weight and/or charged phospholipids such as phosphatidylethanolamine, n-acetylphosphatidylethanolamine or phosphatidic acid in the concentration range 0.1 to 30% by weight.

In contrast to the known aqueous liposomes (vesicles), the phospholipid-stabilised aggregates according to the invention carry in their core hydrophobic fluorocarbons which are capable of the transport of oxygen. Their interfacial chemical stabilisation is effected primarily by a monolayer having inverse arrangement and optionally a structure of bilayer films attached thereto. Because of the peculiarity of their structural arrangement, these novel aggregates are designated as asymmetric lamellar oxygen carriers. Their exceptional colloid chemical stability can presumably be traced back to the lamellar structure and to the surface charge of the aggregates. The latter can be traced back to the choice of suitable phospholipids or their mixtures of natural as well as of synthetic origin. Phospholipids, in particular phosphatidylcholine in the said concentration range from 30 to 99% in combination with lysolecithins of concentration from 0.1 to 10% and/or charged phospholipids in the concentration range 0.1 to 30% by weight are primarily responsible for an advantageous action in this sense. The claimed action of the phospholipids is verified by appropriate negative zeta potentials and by the measurement of charge densities (on titration with a cationic polyelectrolyte).

The advantage of the phospholipid dispersions according to the invention is that as a result of an additional oxygen supply mediated via the fluorocarbon, the circulation and thus the metabolic processes in the epidermal layer is promoted and the general status of breathing of the skin is increased. With the increase in cell respiration, the natural defence potential of the skin is increased and the elimination of skin toxins is promoted. Moreover, as a result of the use of the cosmetic in a phospholipid-stabilised form, the moisture-giving action and skin-smoothing properties associated with it come to bear because of the water-carrying lamellar layer structures.

In contrast to the known preparations mentioned at the beginning, the compositions according to the invention show that the chemically inert fluorocarbons can supply the skin with oxygen advantageously and in metered form on account of their exceptionally high oxygen-dissolving power when used topically in the form of asymmetric lamellar aggregates. It was possible for the first time to confirm the penetration of the asymmetric lamellar aggregates by a spectroscopic process as a confirmation of the effect according to the invention using a labelled phospholipid dispersion of physiologically intact isolated skin.

Use as a cosmetic is not restricted to the face parts of the person, but relates to all epidermal areas of other body, including fatty tissue with deficient circulation affected by cellulitis and the scalp area, in this case in particular the hair cells.

The topical use of fluorocarbon-containing phospholipid-stabilised aggregates on the skin was unknown until now. Fluorocarbons themselves are chemically and biologically inert organic liquids having a high oxygen-dissolving power. Because of these properties, they were proposed as gas carriers in blood substitute emulsions and also put into use in humans (K. C. Lowe: Blood substitutes, Ellis-Horwood, Chichester, GB., 1988). Like soya or egg lecithin, the naturally occurring phospholipids are also toxicologically acceptable and moreover known as skin-compatible and good for the skin.

The fluorocarbons can be selected for $O_2$ solubility, partial vapour pressure and lipid solubility according to the specific intended application. The critical solubility temperature of the fluorocarbons (CST) in n-hexane correlates with their solubility in lipids, e.g. cell membranes, and is thus a measure of the rate of release through the skin. Thus, e.g. perfluorodecalin and perfluorooctyl bromide having small CST values are released relatively rapidly, while on the other hand F-tributylamine having a high CST value of 59° C. also has a high half-life of release. It was found that fluorocarbons behave ideally when mixed and their CST values depend linearly on the composition. It is thus possible by mixing various fluorocarbons to set defined CST values which are often not realisable by means of individual compounds. This result offers the possibility of employing fluorocarbon mixtures specifically to affect the penetration rate into the skin and their residence time in a positive manner.

The invention also relates to a process for the preparation of a phospholipid-containing cosmetic, which consists in emulsifying phospholipids with a fluorocarbon or a fluorocarbon mixture which is loaded with oxygen, the amount of fluorocarbon being in the range from 0.2 to 100% w/v, and the asymmetric lamellar aggregates having a mean particle size from 50 to 3000 nm obtained in this way being incorporated into a carrier suitable for cosmetic use. A preemulsification of the crude dispersion by addition of the fluorocarbon to an aqueous phospholipid solution at a temperature corresponding to the starting substances employed is effected here. The preemulsification is appropriately effected at relatively high speeds of rotation, e.g. 12,000 to 15,000 rpm. The actual homogenisation is then effected using a high-pressure homogeniser. The diameters of the aggregates are in the order of magnitude from 50 to 3000 nm, preferably 140 to 320 nm. The particle size distributions can be rendered uniform or separated by centrifugation. Heat sterilisation in an autoclave is possible without an effect on the particle sizes. To avoid autoxidation processes in the unsaturated fatty acid radical of native lipids, antioxidants, e.g. α-tocopherol, can be added.

The lipid fraction employed according to the process contains phosphatidylcholine according to the invention in an amount from 30–99% by weight based upon the total weight and in particular 70 to 90%.

The incorporation of the asymmetric lamellar aggregates as an active substance in ointments, creams, lotions and other aqueous or alcoholic cosmetic formulations is effected depending on the intended application, it being possible to vary the fluorocarbon content and thus the $O_2$ availability within wide limits. Before incorporation into all cosmetic systems, e.g. gels, pastes, powders, ointments, creams, lotions and waters or alcoholic extracts, the aggregates can be partially loaded or saturated with gaseous oxygen. Even saturation with the oxygen in the atmospheric air by the establishment of equilibrium which customarily takes place according to Henry's law offers a higher oxygen capacity than all comparable known systems.

According to the invention, the content of asymmetric lamellar phospholipid aggregates in the cosmetic preparations can be in the range from 0.05 to 80% by weight, preferably in the range from 0.05 to 60% and in particular in the range from 1 to 50% by weight. It is particularly to be emphasised that, after processing, the asymmetric lamellar phospholipid aggregates according to the invention are present in the cosmetic preparations unaffected by the accompanying substances, which says something for their particular stability.

BRIEF DESCRIPTION OF THE DRAWINGS

The invention will be illustrated in greater detail below by means of examples. In the associated drawings

Figure 1:
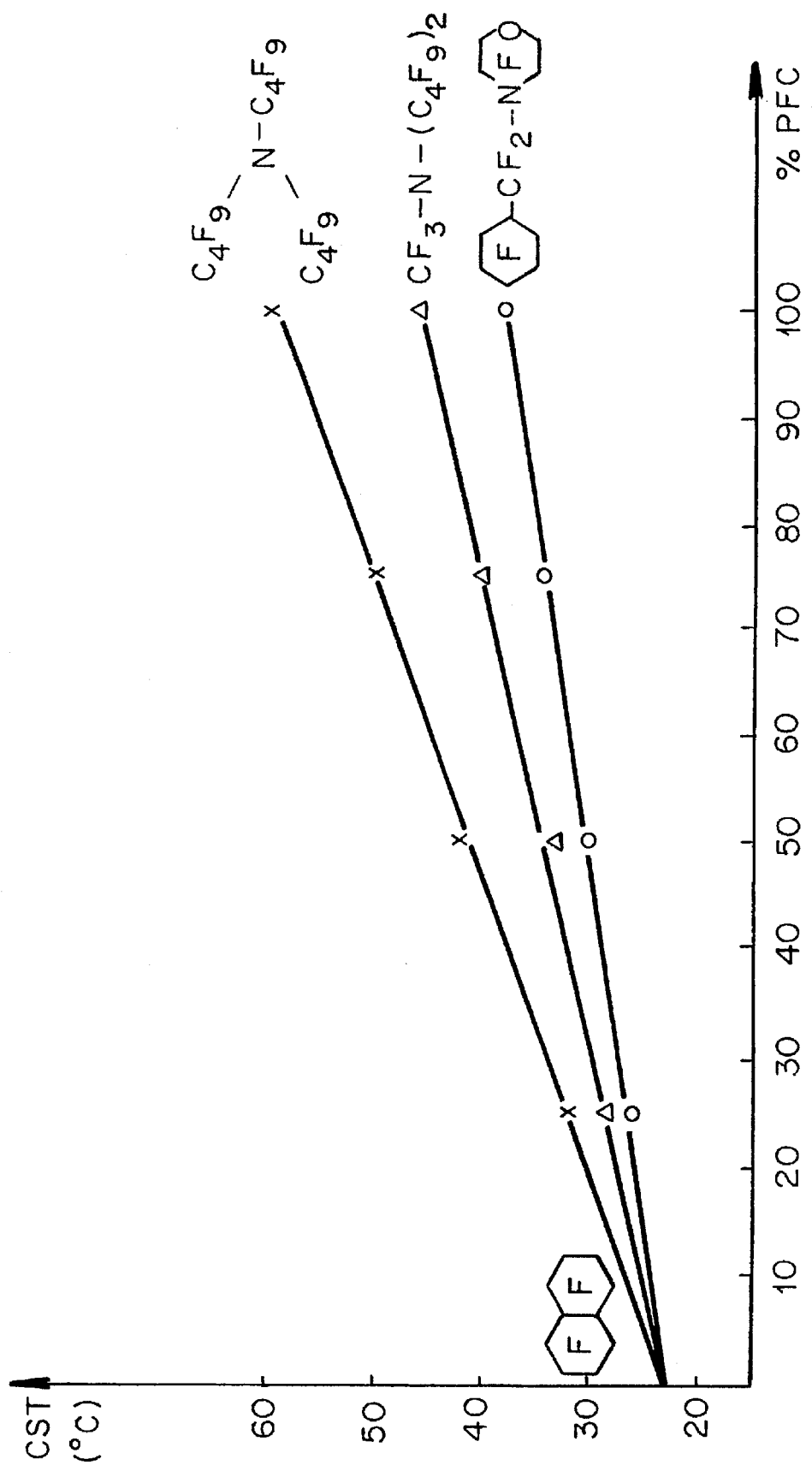
FIG. 1 is a diagram of the critical solubility temperatures (CST) of perfluorocarbon mixtures in n-hexane using perfluorodecalin as a starting point
Figure 2:
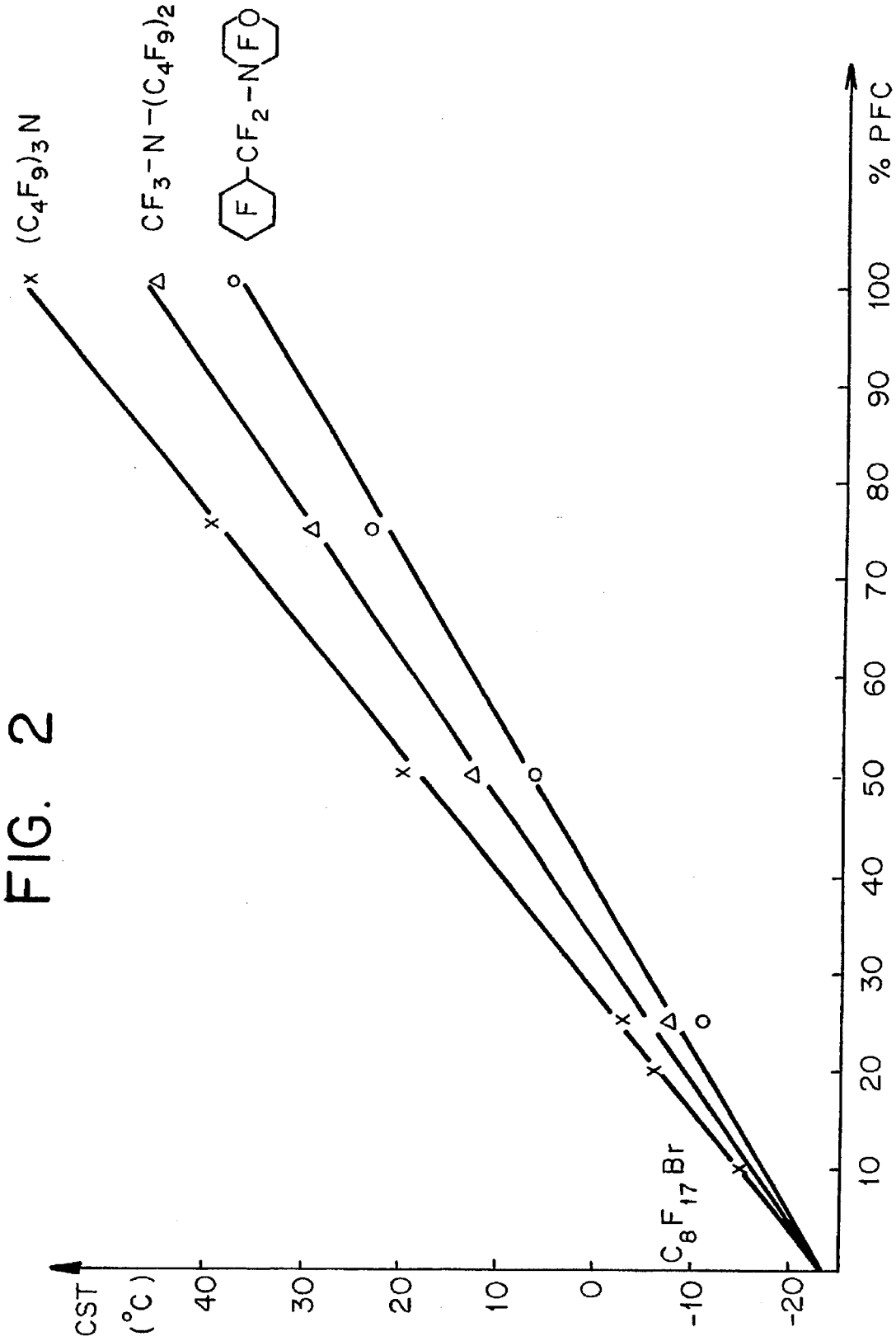
FIG. 2 is a diagram of the critical solubility temperatures of perfluorocarbon mixtures in n-hexane using F-octylbromide as a starting point.

Some selected fluorocarbons and their $O_2$ solubility, their vapour pressure and their critical solubility temperature are shown in Table 1. Starting from these values, the desired characteristics for the penetration of the skin with the aid of a cosmetic composition can be selected for mixtures of fluorocarbons.

TABLE 1

| Fluorocarbon | $O_2$ solubility [ml of $O_2$/100 ml of Fc] | Vapour Pressure $P_{37°\ C.}$ [mm Hg] | CST [°C.] |
| --- | --- | --- | --- |
| Perfluorooctyl bromide | 50 | 14 | −24.5 |
| Perfluorodecalin | 40 | 12.5 | 22 |
| Bis-F(butyl)ethene | 50 | 12.6 | 22.5 |
| F-cyclohexylmethyl-morpholine | 42 | 4 | 38.5 |
| F-tripropylamine | 45 | 18.5 | 43 |
| F-dihexyl ether | 45 | 2 | 59 |
| F-tributylamine | 40 | 1 | 59 |
| Perfluorodecalin-F-tributylamine 1:1 | 40 | 7 | 42 |
| Perfluorobutyl-tetrahydrofuran | 52 | 51 | 29 |
| F-methylcyclohexane | 57 | 180 | 8.2 |
| F-hexane | 58 | 414 | 20 |

EXAMPLE 1

50 ml of a 10% strength aqueous phospholipid solution (soya lecithin, 80% phosphatidylcholine (PC)) are homogenised together with 80 g of a highly pure fluorocarbon mixture containing no H atoms (90% perfluorodecalin, 10% F-dibutylmethylamine, critical solubility temperature 26° C.) using an ultrasonic disintegrator with ice-cooling until the particle size of the particles [sic] have a mean diameter of 244 nm. The multilamellar structure of the aggregates of fluorocarbon and phospholipid can be detected from $^{31}$P-NMR measurements by the typical signal width as well as from electron micrographs.

The aggregation dispersion can be mixed with suitable alcohols for the purpose of sterilisation without problems and without affecting its stability. Addition of 30 ml of ethanol produces sterility, the resulting dispersion having the following composition: 62% w/v fluorocarbons; 9.7% phospholipids; 19% ethanol The zeta potential of minus 61 mV verifies a negative surface charge produced by the phospholipids with an electrostatic stabilisation of the dispersion. After saturation with gaseous oxygen, the dispersion is incorporated into an ointment base which is tolerable and non-interacting with the asymmetric lamellar aggregates. The cosmetic obtained in this way has the following composition:
20 ml of phospholipid dispersion (5 g of fluorocarbon, 2.2 g of phospholipid)
65 ml of aqueous phase (polyacrylic gel, glycerol, polyethylene glycols, methylparaben)
15 ml of oily phase (mineral oil, cetyl alcohol, triglycerides).

The asymmetric lamellar phospholipid aggregates in the cream are unaffected by the accompanying substances.

EXAMPLE 2

18 g of lyophilised phospholipid of the composition [60% PC, 20% PE (phosphatidylethanolamine)] are dissolved in 90 ml of sterilised water and treated with 16 ml of undenatured ethanol. Using a mechanical high-speed stirrer (Ultra-Turrax, 15,000 rpm), the dispersion is stirred and at the same time perfluorodecalin (CST 22° C.) is added successively to the stirring container, which is temperature-controlled at 20° C. The crude dispersion is homogenised at 500 atm in a stream of inert gas in a high-pressure homogeniser of the Manton Gaulin type. At the start of the last but one passage, α-tocopherol acetate is added to 0.1% to the dispersion to avoid autoxidation processes and as a scavenger for free radicals.

The measurements carried out using the photon correlation spectrometer N-4 MD (Coultronics) confirm the presence of a unimodal particle size distribution and a mean particle diameter of 128 nm. The asymmetric lamellar phospholipid aggregates are present in concentrically arranged uneven-numbered layers, as can be clearly detected from cryoelectron micrographs. Electron microscopy investigations using "negative staining" are in agreement with this. According to $^{31}$P-NMR investigations, the asymmetric lamellar aggregates are present in the unilamellar state with a zeta potential of minus 76 mV. The composition of the dispersion is
48% w/v perfluorodecalin
13% phospholipids
9% ethanol

EXAMPLE 3

80 g of n-F-hexane, which is present in a mixture with its perfluorinated isomers (CST 20° C.) were mechanically preemulsified with 9.5 grams of egg yolk 3-sn-phosphatidylcholine in 47 ml of deionised and sterilised water under inert gas conditions with the addition of 0.2% of dl-alpha-tocopherol to give a crude emulsion. The crude emulsion was homogenised in a pressure homogeniser at pressures of 500 atm under a suitable temperature regime and with checking of the particle sizes. The dispersion obtained has a medium viscosity and a particle diameter of 294 nm. After addition of 8 ml of propylene glycol, stability and sterility (microorganism count less than 100 microorganisms/g) were observed in a long-term experiment at room temperature. Dilution, e.g. in the preparation of lotions, is possible without problems without a change of important colloid-chemical parameters.

Investigations of the dispersion in polarised light using a light microscope indicate the presence of an isotropic single phase system, in which liquid-crystalline structures are non-existent.

EXAMPLE 4

In Vivo Detection of Liposome Penetration

A freshly isolated physiologically intact skin was fixed by its inside to an $O_2$ sensor (Clark electrode) and the epidermis was wetted with an $O_2$-transporting dispersion containing asymmetric lamellar aggregates. Under these conditions, the electrode does not indicate an $O_2$ partial pressure. After a penetration period of 57 minutes, the aggregates had reached the dermal skin section in the measuring area of the electrode. The $O_2$ partial pressure rose to a value of 159 mm Hg. The penetration rate into the skin is dependent on the type and size of the aggregates.

EXAMPLES 5 to 19

The following examples describe cosmetic formulations for specific uses. The data in percent contained therein are percentages by weight.

EXAMPLE 5

Emulsion (Body Lotion)

| Polyacrylic acid | 0.30% |
|---|---|
| TEA | 0.30% |
| p-Methylhydroxybenzoate | 0.20% |
| p-Propylhydroxybenzoate | 0.10% |
| Imidazolidinyl urea | 0.20% |
| Na-EDTA | 0.06% |
| Cetyl/siearyl alcohol | 1.00% |
| Stearic acid | 1.00% |
| Isopropyl myristate/palmitate | 3.00% |
| Liquid paraffin | 4.00% |
| Jojoba oil | 2.00% |
| Asymmetric lamellar phospholipid aggregates | 10.00% |
| Perfume oil | 1.00% |
| Demineralised water | q.s. |

EXAMPLE 6

Emulsion (Cream)

| Polyacrylic acid | 0.30% |
|---|---|
| Propylene glycol | 5.00% |
| TEA | 0.30% |
| Emulsifier 1 | 6.00% |
| Emulsifier 2 | 4.50% |
| Aloe vera | 2.00% |
| Rice husk oil | 1.50% |
| Cetyl/stearyl alcohol | 1.00% |

-continued

| | |
|---|---|
| Jojoba oil | 1.50% |
| p-Methylhydroxybenzoate | 0.20% |
| p-Propylhydroxybenzoate | 0.10% |
| Imidazolidinylurea | 0.20% |
| Asymmetric lamellar phospholipid aggregates | 50.00% |
| Perfume oil | 1.00% |
| Demineralised water | q.s. |

EXAMPLE 7

Emulsion (Cleaning Emulsion)

| | |
|---|---|
| Polyacrylic acid | 0.10% |
| Propylene glycol | 3.00% |
| TEA | 0.10% |
| Emulsifier 1 | 5.00% |
| Emulsifier 2 | 2.50% |
| Linalol oil | 1.30% |
| Avocado oil | 2.00% |
| Jojoba oil | 1.50% |
| p-Methylhydroxybenzoate | 0.20% |
| p Propylhydroxybenzoate | 0.10% |
| Imidazolidinylurea | 0.20% |
| Asymmetric lamellar phospholipid aggregates | 0.10% |
| Perfume oil | 0.25% |
| Demineralised water | q.s. |

EXAMPLE 8

Emulsion (Mask)

| | |
|---|---|
| Polyacrylic acid | 0.30% |
| Emulsifier 1 | 5.00% |
| Emulsifier 2 | 6.00% |
| TEA | 0.30% |
| Aloe vera | 1.50% |
| Jojoba oil | 1.50% |
| p-Methylhydroxybenzoate | 0.20% |
| p-Propylhydroxybenzoate | 0.10% |
| Imidazolidinylurea | 0.20% |
| Asymmetric lamellar phospholipid aggregates | 40.00% |
| Perfume oil | 0.50% |
| Demineralised water | q.s. |

EXAMPLE 9

Gel (Gel Mask)

| | |
|---|---|
| Polyacrylic acid | 1.30% |
| Hydroxyethyl cellulose | 0.20% |
| Propylene glycol | 10.00% |
| Asymmetric lamellar phospholipid aggregates | 40.00% |
| TEA | 0.10% |
| p-Methylhydroxybenzoate | 0.20% |
| Imidazolidinylurea | 0.30% |
| Perfume oil | 0.50% |
| Demineralised water | q.s. |

EXAMPLE 10

Sunscreen

| | |
|---|---|
| Emulsifier system consisting of asymmetric | |

-continued

| | |
|---|---|
| lamellar phospholipid aggregates, stabilisers, polyglycerol esters, polyoxyethylene esters, isopropyl palmitate | |
| Glycerol | 5.00% |
| $MgSO_4 \cdot 7H_2O$ | 0.50% |
| UV filter 1 | 3.00% |
| UV filter 2 | 3.00% |
| p-Methylhydroxybenzoate | 0.20% |
| p-Propylhydroxybenzoate | 0.10% |
| Imidazolidinylurea | 0.30% |
| Perfume oil | 1.00% |
| Demineralised water | q.s. |

EXAMPLE 11

Shampoo

| | |
|---|---|
| Sodium lauryl ether sulphate | 35.00% |
| Fatty acid amidoalkyl betaine | 10.00% |
| Pearl lustre concentrate | 5.00% |
| Alkyl amidosulfosuccinate | 5.00% |
| Asymmetric lamellar phospholipid aggregates | 7.50% |
| Luviquat | 1.00% |
| Protein hydrolysate | 1.00% |
| Preservative | 0.40% |
| Citric acid | 0.05% |
| Perfume | 0.50% |
| Rock salt | 0.50% |
| Demineralised water | q.s. |

EXAMPLE 12

Shower Bath

| | |
|---|---|
| Sodium lauryl ether sulphate | 45.00% |
| Fatty acid amidoalkyl betaine | 10.00% |
| Pearl lustre concentrate | 5.00% |
| Asymmetric lamellar phospholipid aggregates | 12.00% |
| Citric acid | 0.05% |
| Preservative | 0.40% |
| Perfume | 1.50% |
| Rock salt | 1.50% |
| Demineralised water | q.s. |

EXAMPLE 13

Hair Treatment

| | |
|---|---|
| Polyacrylic acid | 0.50% |
| Chelaplex | 0.006% |
| TEA | 0.50% |
| Propylene glycol | 6.50% |
| Asymmetric lamellar phospholipid aggregates | 20.00% |
| Preservative | 0.50% |
| Perfume | 1.50% |
| Demineralised water | q.s. |

EXAMPLE 14

Deodorant Cream

| | |
|---|---|
| Emulsifier 1 | 8.00% |
| Emulsifier 2 | 4.00% |
| Jojoba oil | 5.00% |

-continued

| | |
|---|---|
| Aloe vera | 5.00% |
| Propylene glycol | 6.00% |
| Menthol | 0.10% |
| Polyacrylic acid | 0.15% |
| TEA | 0.13% |
| Preservative | 0.50% |
| Asymmetric lamellar phospholipid aggregates | 25.00% |
| Perfume in the deodorant active compound | 1.50% |
| Demineralised water | q.s. |

EXAMPLE 15

Aftershave Balsam

| | |
|---|---|
| Polyacrylic acid | 0.20% |
| Chelaplex | 0.006% |
| TEA | 0.20% |
| Wax | 1.00% |
| Glycerol | 4.00% |
| Jojoba oil | 4.00% |
| Rice husk oil | 4.00% |
| Ethanol | 10.00% |
| Asymmetric lamellar phospholipid aggregates | 37.00% |
| Preservative | 0.50% |
| Perfume | 1.50% |
| Demineralised water | q.s. |

EXAMPLE 16

Make-up

| | |
|---|---|
| Emulsifier system consisting of polyglycerol esters, paraffin, polyoxyethylene esters, isopropyl palmitate, waxes | 25.00% |
| Aloe vera | 2.00% |
| Glycerol | 5.00% |
| $MgSO_4 \cdot 7H_2O$ | 0.50% |
| Preservative | 0.50% |
| Asymmetric lamellar phospholipid aggregates | 37.00% |
| Colorant 1 | 8.50% |
| Perfume oil | 1.00% |
| Demineralised water | q.s. |

EXAMPLE 17

Eye Make-up

| | |
|---|---|
| Carbopol | 0.20% |
| TEA | 0.20% |
| Sorbitol | 10.30% |
| Preservative | 0.50% |
| Liquid paraffin | 2.50% |
| Asymmetric lamellar phospholipid aggregates | 8.00% |
| Emulsifier | 3.70% |
| Mineral oil | 2.90% |
| Ethanol | 5.00% |
| Colorant | 8.00% |
| Demineralised water | q.s. |

EXAMPLE 18

Eyeshadow Compressed with Light Protection Factor

| | |
|---|---|
| Talc | 40.00% |
| Mg carbonate | 1.50% |
| Mg stearate | 2.50% |
| Kaolin | 2.20% |
| Colorants | 15.80% |
| Pearl lustre pigment | 21.50% |
| Perfume oil | 1.50% |
| Silk protein | 5.00% |
| Emulsion as processing means | |
| Emulsifier | 4.50% |
| Silicone oil, volatile | 2.50% |
| Asymmetric lamellar phospholipid aggregates | 2.50% |
| UV filter | 2.00% |
| Preservative | 0.30% |
| Demineralised water | q.s. |

EXAMPLE 19

Make-up—Transparent Powder Compressed with Light Protection Factor

| | |
|---|---|
| Talc | 70.50% |
| Kaolin | 10.00% |
| Mg carbonate | 2.50% |
| Mg stearate | 1.50% |
| Silk protein | 2.50% |
| Colorants | 4.50% |
| Lustre pigments | 7.50% |
| Perfume oil | 1.00% |
| Emulsion as processing means | |
| Emulsifier | 4.50% |
| Silicone oil, volatile | 2.50% |
| Asymmetric lamellar phospholipid aggregates | 2.50% |
| UV Filter | 2.00% |
| Preservative | 0.30% |
| Demineralised water | q.s. |

We claim:

1. Phospholipid-containing and fluorocarbon-containing cosmetic, comprising (a) a carrier suitable for cosmetic use; and (b) asymmetric lamellar aggregates of phospholipids, which have a phosphatidylcholine content in the range from 30% to 99% by weight based upon the total weight, and fluorocarbons laden with oxygen in the range from 0.2% to 100% (weight/volume); and said asymmetric lamellar phospholipid aggregates comprising a central core of fluorocarbons surrounded by at least three layers of phospholipid molecules wherein the layer adjacent to said central core has the lipophilic moiety of the phospholipid interact with the fluorocarbon; and having a skin penetration depending on the critical solubility temperature of the fluorocarbons or fluorocarbon mixtures selected.

2. Cosmetic according to claim 1, wherein the lamellar aggregates have an asymmetric, 3-layer structure, originating from their fluorocarbon core.

3. Cosmetic according to claim 1, wherein the fluorocarbons are selected from the group consisting of aliphatic straight-chain fluoroalkanes and aliphatic branched fluoroalkanes, monocylic fluorocycloalkanes, monocylic fluoroalkyl-substituted fluorocycloalkanes, bicyclic fluorocycloalkanes, bicyclic fluoroalkyl-substituted fluorocycloalkanes, perfluoroinated bicyclic amines, perfluoroinated aliphatic amines, bis(perfluoroalkyl)ethenes, perfluoropolyethers and mixtures thereof.

4. Cosmetic according to claim 3, wherein the fluorocarbons are selected from the group consisting of perfluorodecalin, F-butyltetrahydrofuran, perfluorotributylamine, perfluorooctyl bromide, bisfluoro(butyl)ethene and $C_6$–$C_9$-perfluoroalkanes.

5. Cosmetic according to claim 1, wherein the amount of fluorocarbons is in the range from 20% to 100% weight/volume.

6. Cosmetic according to claim 1, wherein the amount of fluorocarbons is in the range from 40% to 100% weight/volume.

7. Cosmetic according to claim 1, wherein the amount of fluorocarbons is in the range from 70% to 100% weight/volume.

8. Cosmetic according to claim 1, wherein the phospholipids are selected from the group consisting of natural phospholipids, synthetic phospholipids, and the mixtures thereof.

9. Cosmetic according to claim 1, wherein the lipid fraction used contains phosphatidylcholine in an amount from 70% to 99% by weight.

10. Cosmetic according to claim 1, wherein in addition to phosphatidylcholine, lysolecithins are present in the concentration range from 1% to 10% by weight.

11. Cosmetic according to claim 1, wherein said fluorocarbons or fluorocarbon mixtures have a relatively high critical solubility temperature to achieve a slow skin penetration.

12. Process for the preparation of phospholipid-containing and fluorocarbon-containing cosmetic, comprising the steps of incorporating phospholipids having a phosphatidylcholine content in the range from 30% to 99% by weight with a fluorocarbon or fluorocarbon mixture laden with oxygen after pre-emulsification at relatively high rotational speeds and subsequent high-pressure emulsification into a carrier which is suitable for cosmetic use and does not interact with the asymmetric lamellar aggregates; and producing a cosmetic having the amount of fluorocarbon being in the range from 0.2% to 100% (weight/volume) and asymmetric lamellar aggregates having a particle size from 50 to 1000 nm; and said asymmetric lamellar phospholipid aggregates comprising a central core of fluorocarbons surrounded by at least three layers of phospholipid molecules wherein the layer adjacent to said central core has the lipophilic moiety of the phospholipid interact with the fluorocarbon.

13. Process according to claim 12, wherein the fluorocarbons are selected from the group consisting of aliphatic straight-chained fluoroalkanes, branched fluoroalkanes, monocylic fluorocycloalkanes, monocyclic fluoroalkyl-substituted, fluorocycloalkanes, bicyclic fluorocycloalkanes, bicyclic fluoroalkyl-substituted fluorocycloalkanes, perfluorinated aliphatic amines, perfluorinated bicyclic amines, bis(perfluoroalkyl)ethenes, perfluoropolyethers and mixtures thereof.

14. Process according to claim 12, wherein the fluorocarbons are selected from the group consisting of decalin, F-butyltetrahydrofuran, perfluorotributylamine, perfluorooctyl bromide, bisfluoro(butyl)ethene and $C_6$–$C_9$-perfluoroalkanes.

15. Process according to claim 12, wherein the amount of fluorocarbons is in the range from 20% to 100% wt./vol.

16. Process according to claim 12, wherein the amount of fluorocarbons is in the range from 40% to 100% wt./vol.

17. Process according to claim 12, wherein the amount of phospholipids in the cosmetic is in the range from 0.9% to 15% by weight.

18. Process according to claim 12, wherein the amount of phospholipids in the cosmetic is in the range from 2% to 9% by weight.

19. In a method for using a phospholipid-containing cosmetic for control of the oxygen supply to the skin, the improvement which comprises applying a system containing an asymmetric lamellar oxygen carrier, containing phospholipids having a phosphatidylcholine content of 30% to 99% by weight and fluorocarbons in the range from 0.2% to 100% weight/volume, the penetration into the skin being controlled by means of the carrier structure of the phospholipid aggregates and the critical solubility temperature of the fluorocarbons in n-hexane, and the system being distributed in a carrier which is selected from the group consisting of ointment, cream, lotion, water, paste, gel, powder, tincture, a dressing a plaster, and a spray; and said asymmetric lamellar phospholipid aggregates comprising a central core of fluorocarbons surrounded by at least three layers of phospholipid molecules wherein the layer adjacent to said central core has the lipophilic moiety of the phospholipid interact with the fluorocarbon.

20. The method according to claim 19, wherein the content of phosphatidylcholine in the lipid fraction employed is in the range from 30% to 99% by weight.

21. The method according to claim 19, wherein the content of phosphatidylcholine in the lipid fraction employed is in the range from 70% to 90% by weight.

* * * * *